US009879047B2

(12) United States Patent
Obrecht et al.

(10) Patent No.: US 9,879,047 B2
(45) Date of Patent: *Jan. 30, 2018

(54) TEMPLATE-FIXED PEPTIDOMIMETICS

(71) Applicants: UNIVERSITAET ZUERICH, Zurich (CH); POLYPHOR LTD., Allschwil (CH)

(72) Inventors: Daniel Obrecht, Baettwil (CH); Frank Gombert, Binningen (CH); Steven J. Demarco, Diegten (CH); Christian Ludin, Oberwil (CH); Jan Wim Vrijbloed, Moehlin (CH); Kerstin Moehle, Wettswil (CH); John-Anthony Robinson, Wermatswil (CH); Reshmi Mukherjee, Pasadena, CA (US); Heiko Henze, Zurich (CH); Barbara Romagnoli, Binningen (CH)

(73) Assignees: POLYPHOR LTD., Allschwill (CH); UNIVERSITAET ZUERICH, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/379,820

(22) Filed: Dec. 15, 2016

(65) Prior Publication Data
US 2017/0096453 A1  Apr. 6, 2017

Related U.S. Application Data

(63) Continuation of application No. 14/555,796, filed on Nov. 28, 2014, now Pat. No. 9,556,234, which is a continuation of application No. 13/764,099, filed on Feb. 11, 2013, now Pat. No. 8,921,325, which is a continuation of application No. 12/528,926, filed as application No. PCT/CH2007/000101 on Feb. 28, 2007, now Pat. No. 8,399,611.

(51) Int. Cl.
C07K 7/64 (2006.01)
A61K 38/12 (2006.01)
C07K 7/56 (2006.01)
A61K 38/00 (2006.01)

(52) U.S. Cl.
CPC .............. C07K 7/56 (2013.01); A61K 38/12 (2013.01); C07K 7/64 (2013.01); A61K 38/00 (2013.01)

(58) Field of Classification Search
None
See application file for complete search history.

(56) References Cited

U.S. PATENT DOCUMENTS

| 6,878,804 B1 | 4/2005 | Robinson et al. |
| 7,091,313 B2 | 8/2006 | Robinson et al. |
| 7,253,146 B2 | 8/2007 | Obrecht et al. |
| 7,417,024 B2 | 8/2008 | Obrecht et al. |
| 7,582,604 B2 | 9/2009 | Vrijbloed et al. |
| 7,786,078 B2 | 8/2010 | Zumbrunn et al. |
| 7,838,496 B2 | 11/2010 | Zumbrunn et al. |
| 7,855,179 B2 | 12/2010 | Vrijbloed et al. |
| 7,994,118 B2 | 8/2011 | Vrijbloed et al. |
| 8,399,611 B2 | 3/2013 | Obrecht et al. |
| 8,629,112 B2 | 1/2014 | Gombert et al. |
| 8,633,163 B2 | 1/2014 | Obrecht et al. |
| 8,642,560 B2 | 2/2014 | Vrijbloed et al. |
| 8,658,604 B2 | 2/2014 | Demarco et al. |
| 8,685,922 B2 | 4/2014 | Demarco et al. |
| 8,716,242 B2 | 5/2014 | Barthélémy et al. |
| 8,754,038 B2 | 6/2014 | Jung et al. |
| 8,796,183 B2 | 8/2014 | Vrijbloed et al. |
| 8,865,656 B2 | 10/2014 | Obrecht et al. |
| 8,883,720 B2 | 11/2014 | Gombert et al. |
| 8,895,499 B2 | 11/2014 | Obrecht et al. |
| 8,895,695 B2 | 11/2014 | Zumbrunn et al. |
| 8,921,325 B2 | 12/2014 | Obrecht et al. |
| 9,073,973 B2 | 7/2015 | Demarco et al. |
| 9,079,939 B2 | 7/2015 | Obrecht et al. |
| 9,109,009 B2 | 8/2015 | Gombert et al. |
| 9,284,352 B2 | 3/2016 | Obrecht et al. |
| 9,512,139 B2 | 12/2016 | Obrecht et al. |
| 9,518,092 B2 | 12/2016 | Zumbrunn et al. |
| 9,521,846 B2 | 12/2016 | Demarco et al. |
| 9,538,752 B2 | 1/2017 | Demarco et al. |
| 9,556,231 B2 | 1/2017 | Obrecht et al. |
| 9,556,234 B2 | 1/2017 | Obrecht et al. |
| 9,596,852 B2 | 3/2017 | Demarco et al. |

(Continued)

FOREIGN PATENT DOCUMENTS

| WO | 01 16161 | 3/2001 |
| WO | 02 070547 | 9/2002 |
| WO | 2004 096840 | 11/2004 |

OTHER PUBLICATIONS

Burger et al., "CXCR4 antagonists: targeting the microenvironment in leukemia and other cancers", Leukemia, 2009, 43-52.*
Burger et al., "CXCR4: a key receptor in the crosstalk between tumor cells and their microenvironment", Blood, 2006, 1761-1676;published online Nov. 3, 2005.*
Haviv et al., "Transcriptional targeting in renal cancer cell lines via the human CXCR4 promoter", Molecular Cancer Therapeutics, 2004; 687-691.*
Rubin et al., "A small-molecule antagonist of CXCR4 inhibits intracranial growth of primary brain tumors", PNAS, 2003, 13513-13518.*
Demarco Steven J. et al., "Discovery of novel, highly potent and selective β-hairpin mimetic CXCR4 inhibitors with excellent anti-HIV activity and pharmacokinetic profiles", Bioorganic & Medicinal Chemistry, vol. 14, No. 24, pp. 8396-8404, XP002429454, Dec. 15, 2006.

(Continued)

Primary Examiner — Lianko G Garyu
(74) Attorney, Agent, or Firm — Oblon, McClelland, Maier & Neustadt, L.L.P.

(57) ABSTRACT

The template-fixed β-hairpin peptidomimetics Cyclo(-Tyr-His-Cys-Ser-Ala-$^D$Pro-Dab-Arg-Tyr-Cys-Tyr-Gln-Lys-$^D$-Pro-Pro), disulfide bond between Cys4 and Gys11, and pharmaceutically acceptable salts thereof, with X being Ala or Tyr, have CXCR4 antagonizing properties and can be used for where cancer is mediated or resulting from CXCR4 receptor activity.

4 Claims, 2 Drawing Sheets

(56) References Cited

U.S. PATENT DOCUMENTS

| | | |
|---|---|---|
| 2004/0171066 A1 | 9/2004 | Obrecht et al. |
| 2006/0293286 A1 | 12/2006 | Erickson et al. |
| 2007/0078079 A1 | 4/2007 | Zumbrunn et al. |
| 2010/0056432 A1 | 3/2010 | Vrijbloed et al. |
| 2011/0135576 A1 | 6/2011 | Demarco et al. |
| 2011/0230426 A1 | 9/2011 | Obrecht et al. |
| 2011/0245155 A1 | 10/2011 | Zumbrunn et al. |
| 2011/0312879 A1 | 12/2011 | Gombert et al. |
| 2011/0319291 A1 | 12/2011 | Vrijbloed et al. |
| 2012/0135942 A1 | 5/2012 | Obrecht et al. |
| 2012/0202821 A1 | 8/2012 | Obrecht et al. |
| 2012/0270881 A1 | 10/2012 | Obrecht et al. |
| 2012/0283168 A1 | 11/2012 | Jung et al. |
| 2012/0283196 A1 | 11/2012 | Barthélémy et al. |
| 2013/0189363 A1 | 7/2013 | Obrecht et al. |
| 2013/0225506 A1 | 8/2013 | Gombert et al. |
| 2014/0087994 A1 | 3/2014 | Demarco et al. |
| 2014/0107031 A1 | 4/2014 | Obrecht et al. |
| 2014/0187471 A1 | 7/2014 | Demarco et al. |
| 2014/0187472 A1 | 7/2014 | Demarco et al. |
| 2014/0213509 A1 | 7/2014 | Obrecht et al. |
| 2014/0213531 A1 | 7/2014 | Demarco et al. |
| 2014/0287986 A1 | 9/2014 | Jung et al. |
| 2014/0364583 A1 | 12/2014 | Obrecht et al. |
| 2015/0051183 A1 | 2/2015 | Obrecht et al. |
| 2015/0216927 A1 | 8/2015 | Dale et al. |
| 2015/0218219 A1 | 8/2015 | Gombert et al. |
| 2015/0224168 A1 | 8/2015 | Dale et al. |
| 2015/0307556 A1 | 10/2015 | Gombert et al. |
| 2016/0052971 A1 | 2/2016 | Obrecht et al. |
| 2016/0060298 A1 | 3/2016 | Obrecht et al. |
| 2016/0318976 A1 | 11/2016 | Gombert et al. |
| 2016/0333051 A1 | 11/2016 | Demarco et al. |
| 2016/0333053 A1 | 11/2016 | Gombert et al. |

OTHER PUBLICATIONS

Tamamura, Hirokazu et al., "Development of Specific CXCR4 Inhibitors Possessing High Selectivity Indexes as Well as Complete Stability in Serum Based on an Anti-HIV Peptide T140", Bioorganic & Medicinal Chemistry Letters, vol. 11, No. 14, pp. 1897-1902, XP002265743, Jul. 23, 2001.

Tamamura, Hirokazu et al., "Development of Anti-HIV Agents Targeting Dynamic Supramolecular Mechanism: Entry and Fusion Inhibitors Based on CXCR4/CCR5 Antagonists and gp41-C34-Remodeling Peptides", Current HIV Research, vol. 3, No. 4, pp. 289-301, XP008077509, Oct. 2005.

Abdel-Rahman et al., "HIV Protease Inhibitors: Peptidomimetic Drugs and Future Perspectives", 2009, Current Medicinal Chemistry, pp. 1905-1922.

Stevenson, "Advances in Peptide Pharmaceuticals", 2009, Current Pharmaceutical Biotechnology, pp. 122-137.

Obrecht, D. et al., "B-Hairpin protein epitope mimetic technology in drug discovery", 2011, Drug Discov Today: Technol, pp. e1-e7.

U.S. Appl. No. 15/444,045, filed Feb. 27, 2017, Gombert, et al.

\* cited by examiner

TEMPLATE-FIXED PEPTIDOMIMETICS

CROSS-REFERENCE TO RELATED APPLICATIONS

This is a continuation of U.S. application Ser. No. 14/555,796, filed Nov. 28, 2014, which is a continuation of U.S. application Ser. No. 13/764,099, filed Feb. 11, 2013, now U.S. Pat. No. 8,921,325, which is a continuation of U.S. application Ser. No. 12/528,926, filed Oct. 27, 2009, now U.S. Pat. No. 8,399,611, which is the National Stage of International application no. PCT/CH2007/00101, filed Feb. 28, 2007, of which all of the disclosures are incorporated herein by reference in their entireties.

JOINT RESEARCH AGREEMENT

The claimed invention was made by, on behalf of, and/or in connection with one or more of the following parties to a joint university corporation research agreement: Universitaet Zuerich and Polyphor Ltd. The agreement was in effect on and before the date the claimed invention was made, and the claimed invention was made as a result of activities undertaken within the scope of the agreement.

FIELD OF THE INVENTION

The present invention provides template-fixed β-hairpin peptidomimetics which are having CXCR4 antagonizing activity and are embraced by the general disclosure of, but not specifically disclosed in WO2004/096840 A1.

SUMMARY OF THE INVENTION

The 13-hairpin peptidomimetics of the invention are Cyclo(-Tyr-His-X-Cys-Ser-Ala-$^D$Pro-Dab-Arg-Tyr-Cys-Tyr-Gln-Lys-$^D$Pro-Pro), disulfide bond between Cys4 and Cysl 1, and pharmaceutically acceptable salts thereof, with X being Ala or Tyr.

DETAILED DESCRIPTION OF THE INVENTION

Figure 1:
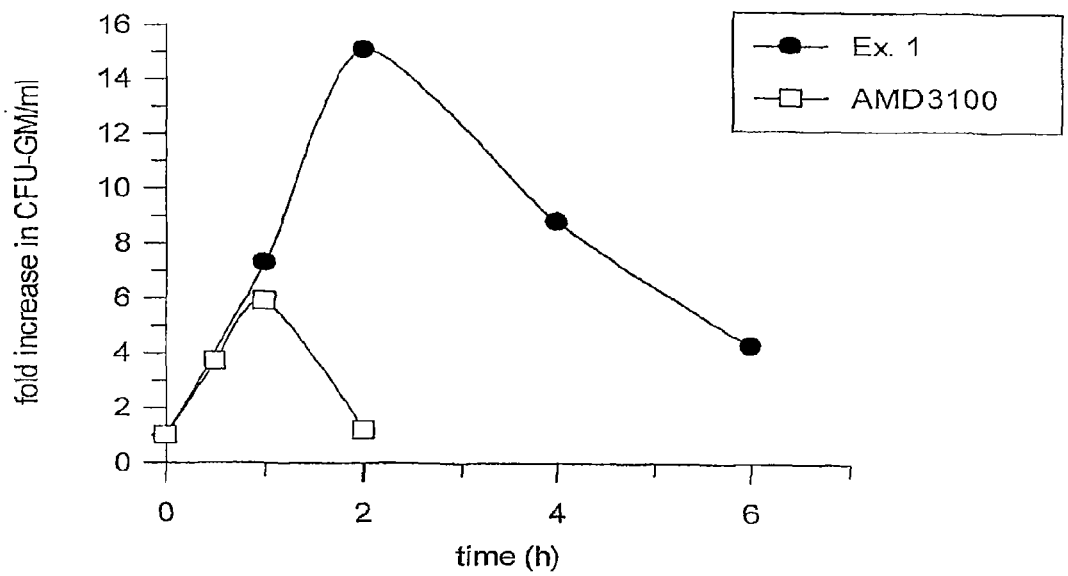
FIG. 1. Increase in Colony Forming Units per ml of blood (CFU-GM) over time for both the compound of Example I (5 mg) and the reference compound AMD3100.

In accordance with the invention, the aforesaid β-hairpin mimetics and pharmaceutically acceptable salts thereof can be prepared by a process which comprises
(a) coupling an appropriately functionalized solid support with an appropriately N-protected derivative of Pro;
(b) removing the N-protecting group from the product obtained in step (a);
(c) coupling the product thus obtained with an appropriately N-protected derivative of $^D$Pro;
(d) removing the N-protecting group from the product thus obtained;
(e) coupling the product thus obtained with an appropriately N-protected derivative of the amino acid which in the desired end-product is in position 14, i.e. Lys, the amino group present in its side-chain being likewise appropriately protected;
(f) removing the N-protecting group from the product thus obtained;
(g) effecting steps substantially corresponding to steps (e) and (f) using appropriately N-protected derivatives of the amino acids which in the desired end-product are in positions 13 to 1, i.e. Gln, Tyr, Cys, Tyr, Arg, Dab, $^D$Pro, Ala, Ser, Cys, Ala or Tyr, His and Tyr, any functional group which may be present in said N-protected amino acid derivatives being likewise appropriately protected;
(h) forming the disulfide β-strand linkage between the side-chains of the Cys residues in positions 4 and 11;
(i) detaching the product thus obtained from the solid support;
(j) cyclizing the product cleaved from the solid support;
(k) removing any protecting groups present on functional groups of any members of the chain of amino acid residues; and
(l) if desired, converting the product thus obtained into a pharmaceutically acceptable salt or converting a pharmaceutically acceptable, or unacceptable, salt thus obtained into the corresponding free compound or into a different, pharmaceutically acceptable, salt.

The steps of the aforesaid process can be carried out by methods which are well known to any person adequately skilled in peptide chemistry.

The β-hairpin peptidomimetics of the invention can be used in a wide range of applications for preventing HIV infections in healthy individuals or for slowing and halting viral progression in infected patients; or where cancer is mediated or resulting from CXCR4 receptor activity; or where immunological diseases are mediated or resulting from CXCR4 receptor activity; or for treating immuno suppression; or for treating inflammation, or, in particular, for stem cell mobilisation of peripheral blood stem cells and/or mesenchymal stem cell (MSC) and/or other stem cells which retention depend on the CXCR4-receptor.

The β-hairpin peptidomimetics of the invention may be administered per se or may be applied as an appropriate formulation together with carriers, diluents or excipients well known in the art.

In particular, the β-hairpin peptidomimetics of the invention can be used as a treatment to increase hematopoetic stem cell (HSC) release from the bone marrow to be used in allogenic or autologous transplant.

The acute treatment with infused HSC is widely used to restore immune functions in patients who have received myeloablative therapy during the treatment of malignancies such as multiple myeloma and non-Hodgkin's lymphoma. Patients or donors are treated with the HCS mobilisation agent, such as a compound of the invention, and the cells are subsequently collected from peripheral blood by apharesis. HCS are transplanted back after e.g. chemotherapy treatment into the patient (autologous transplant) or from donor to recipient (allogenic transplant), thus promoting the restoration of immune function (Frühauf et al., Br. J. Haematol. 122, 360-375 (2003)).

Other applications of the HSC treatment include, but are not limited to, therapeutic angiogenesis in case of e.g. heart attack (Shepherd R M et al, *Blood* 2006 108(12):3662-3667).

The β-hairpin peptidomimetics of the invention may also be used to treat or prevent HIV infections or cancer such as breast cancer, brain cancer, prostate cancer, lung cancer, kidney cancer, neuroblastoma, non-Hodgkin's lymphoma, ovarian cancer, multiple myeloma, chronic lyphomphocytic leukemia, pancreatic cancer, melanoma, angiogenesis and haematopoetic tissues; or inflammatory disorders such as asthma, allergic rhinitis, hypersensitivity lung diseases, hypersensitivity pneumonitis, eosinophilic pneumonias, delayed-type hypersensitivity, interstitial lung disease (ILD), idiopathic pulmonary fibrosis, ILD associated with rheumatoid arthritis, systemic lupus erythematosus, ankylosing spondylitis, peripheral vascular disease, systemic sclerosis, Sjogren's syndrome, von Hippel Lindau disease, systemic anaphylaxis or hypersensitivity responses, drug allergies, rheumatoid arthritis, psoriatic arthritis, Behcet's Syndrome, mucositis, Crohn's disease, multiple sclerosis, myasthenia gravis, juvenile onset diabetes, glomerulonephritis, autoimmune throiditis, graft rejection, including allograft rejection or graft-versus-host disease, inflammatory bowel diseases, inflammatory dermatoses; or to treat immunosuppression, including immunosuppression induced by graft/transplantation rejection.

The β-hairpin peptidomimetics of the invention can be administered singly, as mixtures of more than one β-hairpin peptidomimetics, in combination with, as the case may be, other HSC mobilisation agents, or anti-HIV agents, or antimicrobial agents, or anti cancer agents, or anti-inflammatory agents, and/or in combination with other pharmaceutically active agents.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hank's solution, Ringer's solution, or physiological saline buffer. The solutions may contain formulatory agents such as suspending, stabilizing and/or dispersing agents.

Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion by a patient to be treated. For oral formulations such as, for example, powders, capsules and tablets, suitable excipients include fillers such as sugars, e. g. lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose; granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide may also be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin peptidomimetics of the invention contain charged residues, they may be included in any of the above-described formulations as such or as pharmaceutically acceptable salts. Pharmaceutically acceptable salts tend to be more soluble in aqueous and other protic solvents than are the corresponding free forms. Particularly suitable pharmaceutically acceptable salts include salts with, carboxylic, phosphonic, sulfonic and sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, and other organic protonic acids, such as ascorbic acid. Suitable inorganic acids are, for example, hydrohalic acids, such as hydrochloric acid, sulfuric acid, and phosphoric acid.

The β-hairpin peptidomimetics of the invention, in free form or in the form of pharmaceutically acceptable salts, or compositions thereof, will generally be used in an amount effective to achieve the intended purpose. It is to be understood that the amount used will depend on a particular application.

For topical administration to treat or prevent HIV infections a therapeutically effective dose can be determined using, for example, the in vitro assays provided in the examples. The treatment may be applied while the HIV infection is visible, or even when it is not visible. An ordinary skilled expert will be able to determine therapeutically effective amounts to treat topical HIV infections without undue experimentation.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture). Such information can be used to more accurately determine useful doses in humans.

Initial dosages can also be determined from in vivo data, e.g. animal models, using techniques that are well known in the art. One having ordinary skill in the art could readily optimize administration to humans based on animal data.

Dosage amounts for applications as anti-HIV agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the ordinary skill in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The anti-HIV therapy may be repeated intermittently while infections are detectable or even when they are not detectable. The therapy may be provided alone or in combination with other drugs, such as for example other anti-HIV agents or anti cancer agents, or other antimicrobial agents.

Normally, a therapeutically effective dose of the β-hairpin peptidomimetics described herein will provide therapeutic benefit without causing substantial toxicity.

Toxicity of the β-hairpin peptidomimetics of the invention can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, in: *The Pharmacological Basis of Therapeutics*, Ch. 1, p. 1).

The following Examples illustrate the invention in more detail but are not intended to limit its scope in any way. The following abbreviations are used in these Examples:

HBTU: 1-benzotriazol-1-yl-tetramethyluronium hexafluorophosphate (Knorr et al. *Tetrahedron Lett.* 1989, 30, 1927-1930);
HOBt: 1-hydroxybenzotriazole;
DMA: diisopropylethylamine;
HOAT: 7-aza-1-hydroxybenzotriazole;
HATU: O-(7-aza-benzotriazole-1-yl)-N,N,N',N'-tetramethyluronium hexafluorophosphate (Carpino et al. *Tetrahedron Lett.* 1994, 35, 2279-2281).

1. Peptide Synthesis

Coupling of the First Protected Amino Acid Residue to the Resin 0.5 g of 2-chlorotritylchloride resin (100-200 mesh, copoly(styrene-1% DVB) polymer matrix, Cat. No. 01-64-0114, Novabiochem, Merck Biosciences Ltd.) (Barlos et al. *Tetrahedron Lett.* 1989, 30, 3943-3946) (1.4 mMol/g, 0.7 mmol) was filled into a dried flask. The resin was suspended in $CH_2Cl_2$ (2.5 ml) and, allowed to swell at room temperature under constant stirring for 30 min. The resin was treated with 0.49 mMol (0.7 eq) of the first suitably protected amino acid residue and 488 µl (4 eq) of diisopropylethylamine (DIEA) in $CH_2Cl_2$ (2.5 ml), the mixture was shaken at 25° C. for 4 hours. The resin was shaken ($CH_2Cl_2$/MeOH/DIEA: 17/2/1), 30 ml for 30 min; then washed in the following order with $CH_2Cl_2$ (1×), DMF (1×), $CH_2Cl_2$ (1×), MeOH (1×), $CH_2Cl_2$ (1×), MeOH (1×), $CH_2Cl_2$ (2×), $Et_2O$ (2×) and dried under vacuum for 6 hours.

Loading was typically 0.6-0.9 mMol/g.

The following preloaded resin was prepared: Fmoc-Pro-2-chlorotritylresin.

Synthesis of the Fully Protected Peptide Fragment

The synthesis was carried out on a Syro-peptide synthesizer (MultiSynTech GmbH) using 24 to 96 reaction vessels. In each vessel were placed approximately 60 mg (weight of the resin before loading) of the above resin. The following reaction cycles were programmed and carried out:

| Step | Reagent | Time |
| --- | --- | --- |
| 1 | $CH_2Cl_2$, wash and swell (manual) | 1 × 3 min. |
| 2 | DMF, wash and swell | 1 × 60 min. |
| 3 | 40% piperidine/DMF | 2 × 5 min. |
| 4 | DMF, wash | 5 × 1 min. |

-continued

| Step | Reagent | Time |
|---|---|---|
| 5 | 5 equiv. Fmoc amino acid/DMF + 5 eq. HBTU + 10 eq. DIEA | 2 × 60 min. |
| 6 | DMF, wash | 5 × 1 min. |
| 7 | 40% piperidine/DMF | 2 × 5 min. |
| 8 | DMF, wash | 5 × 1 min. |
| 9 | $CH_2Cl_2$, wash (at the end of the synthesis) | 3 × 1 min. |

Steps 3 to 6 are repeated to add each amino-acid.

Analytical Method:

Analytical HPLC retention times (RT, in minutes) were determined using a Jupiter Proteo 90 A column, 150×2.0 mm, (cod. 00F-4396-B0-Phenomenex) with the following solvents A ($H_2O$+0.1% TFA) and B ($CH_3CN$+0.1% TFA) and the gradient: 0 min: 95% A, 5% B; 0.5 min: 95% A, 5% B; 20 min: 40% A, 60% B; 21 min: 0% A, 100% B; 23 min: 0% A, 100% B; 23.1 min: 95% A, 5% B; 31 min: 95% A, 5% B.

Formation of Disulfide β-Strand Linkage

After completion of the synthesis, the resin was swelled in 3 ml of dry DMF for 1 h. Then 10 eq. of iodine solution in DMF (6 ml) were added to the reactor, followed by stirring for 1.5 h. The resin was filtered and a fresh solution of iodine (10 eq.) in DMF (6 nil) was added, followed by stirring for another 3 h. The resin was filtered and washed with DMF (3×) and $CH_2Cl_2$(3×).

Cleavage, Backbone Cyclization, Deprotection and Purification of the Peptide

After formation of the disulfide β-strand linkage, the resin was suspended in 1 ml (0.14 mMol) of 1% TFA in $CH_2Cl_2$ (v/v) for 3 minutes and filtered, and the filtrate was neutralized with 1 ml (1.15 mMol) of 20% DIEA in $CH_2Cl_2$ (v/v). This procedure was repeated twice to ensure completion of the cleavage. The resin was washed three times with 1 ml of $CH_2Cl_2$. The $CH_2Cl_2$ layer was evaporated to dryness.

The volatiles were removed and 8 ml dry DMF were added to the tube. Then 2 eq. of HATU in dry DMF (1 ml) and 4 eq. of DIPEA in dry DMF (1 ml) were added to the peptide, followed by stirring for 16 h. The volatiles were evaporated to dryness. The crude cyclised peptide was dissolved in 7 ml of $CH_2Cl_2$ and extracted with 10% acetonitrile in $H_2O$ (4.5 ml) three times. The $CH_2Cl_2$ layer was evaporated to dryness. To deprotect the peptide fully, 3 ml of cleavage cocktail TFA:TIS:$H_2O$ (95:2.5:2.5) were added, and the mixture was kept for 2.5 h. The volatiles were evaporated to dryness and the crude peptide was dissolved in 20% AcOH in water (7 ml) and extracted with isopropyl ether (4 ml) for three times. The aqueous layer was collected and evaporated to dryness, and the residue was purified by preparative reverse phase HPLC.

After lyophilisation the products were obtained as white powders and analysed by the HPLC-ESI-MS analytical method described above. The analytical data comprising purity after preparative HPLC and ESI-MS are given.

EXAMPLE 1

The peptide was synthesized starting with the amino acid L-Pro which was grafted to the resin. Starting resin was Fmoc-Pro-2-chlorotrityl resin, which was prepared as described above. The linear peptide was synthesized on solid support according to the procedure described above in the following sequence: Resin-Pro-$^D$Pro-Lys-Gln-Tyr-Cys-Tyr-Arg-Dab-$^D$Pro-Ala-Ser-Cys-Ala-His-Tyr. A disulfide β-strand linkage was introduced as described above. The product was cleaved from the resin, cyclized, deprotected and purified as indicated by preparative reverse phase LC-MS.

After lyophilisation the product was obtained as white powder and analysed by the HPLC-ESI-MS analytical method described above ([M+2H]$^{2+}$: 933.1; RT: 10.47; UV-purity: 72%).

EXAMPLE 2

The peptide was synthesized starting with the amino acid L-Pro which was grafted to the resin. Starting resin was Fmoc-Pro-2-chlorotrityl resin, which was prepared as described above. The linear peptide was synthesized on solid support according to the procedure described above in the following sequence: Resin-Pro-$^D$Pro-Lys-Gln-Tyr-Cys-Tyr-Arg-Dab-$^D$Pro-Ala-Ser-Cys-Tyr-His-Tyr. A disulfide β-strand linkage was introduced as described above. The product was cleaved from the resin, cyclized, deprotected and purified as indicated by preparative reverse phase LC-MS. After lyophilisation the product was obtained as white powder and analysed by the HPLC-ESI-MS analytical method described above ([M+2H]$^{2+}$: 978.6; RT: 10.95; UV-purity: 82%).

2. Biological Methods 2.1. Preparation of the Peptides.

Lyophilized peptides were weighed on a Microbalance (Mettler MT5) and dissolved in sterile water to a final concentration of 1 mM unless stated otherwise. Stock solutions were kept at +4° C., light protected.

2.2. $Ca^{2+-}$ Assay: CXCR4-Antagonizing Activity of the Peptides.

Increases in intracellular calcium were monitored using a Flexstation 384 (Molecular Devices, Sunnyvale, Calif.) to assay the peptides for CXCR4 antagonism in a mouse pre-B cell line 300-19 stably transfected with human CXCR4 [see references 1, 2 and 3, below]. The cells were batch loaded with the Calcium 3 Assay kit (Molecular Devices) in assay buffer (Hanks Balanced salt solution, HBSS, 20 mM HEPES, pH 7.4, 0.1% BSA) for 1 h at room temperature and then 200,000 labeled cells were dispensed into black 96 well assays plates (Costar No. 3603). A 20-fold concentrated solution of peptide in assay buffer was added to the cells and the whole plate was centrifuged to settle the cells to the bottom of the wells. Calcium mobilization induced by 10 nM stromal-derived factor-1 (SDF-1) was measured in the Flexstation 384 (excitation, 485 nM; emission, 525 nM) for 90 seconds. A maximal change in fluorescence response above baseline was used to calculate antagonist activity. The data for dose response curves (antagonist concentration versus % maximum response) were fitted to a four parameter logistic equation using SoftmaxPro 4.6 (Molecular Devices), from which $IC_{50}$% values were calculated.

2.3. FIGS-Assay™

The assay was performed according to ref. 5, below. Stock dilutions of the peptides (10 μM) were prepared by dissolving in 10 μM Tris-HCl at room temperature. Stock solutions were kept at +4° C., light protected. Working dilutions were prepared extemporaneously by serial dilution in Phosphate Buffered Saline (PBS) and added in a final volume of 10 μl directly to the cell cultures. After 48 hours of co-cultivation the cultures were rinsed with PBS and then exposed to glutaraldehyde/formaldehyde (0.2%/2%) in PBS for five minutes. For photometric quantification the fixed cultures were subsequently incubated with ortho-nitro-phenyl-galactopyranoside (ONPG) as a β-galactosidase substrate, which was enzymatically converted into the chromophore orthonitrophenol (ONP). The read out is directly obtained by measuring optical density of wells at 405 nm in an iEMS 96 well-plate reader.

2-4. Cytotoxicity Assay

The cytotoxicity of the peptides to HFLA cells (Acc57) and COS-7 cells (CRL-1651) was determined using the MTT reduction assay [see ref. 6 and 7, below]. Briefly the method was as follows: HELA cells and COS-7 cells were seeded at $7.0 \times 10^3$ and, respectively, $4.5 \times 10^3$ cells per well and grown in 96-well microtiter plates for 24 hours at 37° C. at 5% $CO_2$. At this point, time zero (Tz) was determined by MTT reduction (see below). The supernatant of the remaining wells was discarded, and fresh medium and the peptides in serial dilutions of 12.5, 25 and 50 μM were pipetted into the wells. Each peptide concentration was assayed in triplicate. Incubation of the cells was continued for 48 hours at 37° C. at 5% $CO_2$. Wells were then washed once with PBS and subsequently 100 μl MTT reagent (0.5 mg/mL in medium RPMI1640 and, respectively, DMEM) was added to the wells. This was incubated at 37° C. for 2 hours and subsequently the medium was aspirated and 100 μl isopropanol was added to each well. The absorbance at 595 nm of the solubilized product was measured ($OD_{595}$peptide). For each concentration averages were calculated from triplicates. The percentage of growth was calculated as follows: ($OD_{595}$peptide–$OD_{595}$Tz–$OD_{595}$Empty well)/($OD_{595}$Tz–$OD_{595}$Empty well)×100% and was plotted for each peptide concentration.

The LC 50 values (Lethal Concentration, defined as the concentration that kills 50% of the cells) were determined for each peptide by using the trend line function of EXCEL (Microsoft Office 2000) for the concentrations (50, 25, 12.5 and 0 μM), the corresponding growth percentages and the value −50, (=TREND($C_{50}$:$C_0$%50:%0,−50)). The GI 50 (Growth Inhibition) concentrations were calculated for each peptide by using a trend line function for the concentrations (50, 25, 12.5 and 0 μg/ml), the corresponding percentages and the value 50, (=TREND ($C_{50}$:$C_0$,%50:%0,50).

2.5. Cell Culture

'CCR5' cells were cultured in DMEM medium with 4500 mg/ml glucose, 10% fetal bovine serum (FBS), supplemented with 50 U/ml Penicillin and 50 μg/ml Streptomycin (Pen/Strept.). Hut/4-3 cells were maintained in RPMI medium, 10% FBS, supplemented with Pen/Strept. and 10 mM HEPES. HFLA cells and CCRF-CEM cells were maintained in RPMI1640 plus 5% FBS, Pen/Strept and 2 mM L-Glutamine. Cos-7 cells were grown in DMEM medium with 4500 mg/ml glucose supplemented with 10% FCS, Pen/Strept. and 2 mM L-Glutamine. All cell lines were grown at 37° C. at 5% $CO_2$. Cell media, media supplements, PBS-buffer, HEPES, Pen/Strept., L-Glutamine and sera were purchased from Gibco (Pailsey, UK). All fine chemicals came from Merck (Darmstadt, Germany).

2.6. Hemolysis

The peptides were tested for their hemolytic activity against human red blood cells (hRBC). Fresh hRBC were washed three times with phosphate buffered saline (PBS) by centrifugation for 10 min at 2000×g. Peptides at a concentration of 100 μM were incubated with 20% v/v hRBC for 1 hour at 37° C. The final erythrocyte concentration was approximately $0.9 \times 10^9$ cells per ml. A value of 0% resp. 100% cell lysis was determined by incubation of the hRBC in the presence of PBS alone and respectively 0.1% Triton X-100 in $H_2O$. The samples were centrifuged and the supernatant was 20-fold diluted in PBS buffer and the optical density (OD) of the sample at 540 nM was measured. The 100% lyses value ($OD_{540}H_2O$) gave an $OD_{540}$ of approximately 1.3-1.8. Percent hemolysis was calculated as follows: ($OD_{540}$peptide/$OD_{540}H_2O$)×100%.

2.7. Chemotactic Assay (Cell Migration Assay)

The chemotactic response of CCRF-CEM cells to a gradient of stromal cell-derived factor 1α (SDF-1) was measured using disposable assay plates from Neuroprobe (5μ pore size) (Gaithersburg, Md.), according to the manufacturer's directions and references therein [especially ref. 8, below]. Briefly, one 175 $cm^3$ flask was washed once with Dubecco's phosphate buffered saline (DPBS), and trypsinized for 10 minutes or until cells had lifted. The trypsin was neutralized by the addition of fresh medium containing serum and the cells were pelleted, washed once in DPBS, and resuspended at $1-0.5 \times 10^7$ cells/ml in RPMI+ 0.5% bovine serum albumin (BSA). 45 μl of cell suspension were mixed with 5 μl of 10-fold concentrated PEM peptide diluted in the same assay medium. 35 μl of this mixture were applied to the top of the assay filter. The cells were allowed to migrate (at 37°) into the bottom chamber of the assay plate containing 1 nM SDF-1. After 4 hours, the filter was removed and MTT was added to the migrated cells to a final concentration of 0.5 mg/ml, and incubated for a further 4 hours. After labeling with MTT, all medium was removed and 100 μl of isopropanol+10 mM HCl were added to the cells. The optical absorbance at 595 nm ($ABS_{595}$) was read using a Tecan Genios plate reader with Magellan software. The number of cells migrated was determined by comparing $ABS_{595}$ values against a standard curve generated with a known number of cells in the assay plate and were plotted against SDF-1 concentration to obtain a sigmoidal curve and to determine the $IC_{50}$ values. The values for IC50 were determined using the Trendline function in Microsoft Excel by fitting a logarithmic curve to the averaged datapoints.

2.8 Plasmastability

405 μl of plasma/albumin solution were placed in a polypropylene (PP) tube and spiked with 45 μl of compound from a 100 μM solution B, derived from 135 μl of PBS and 15 μl of 1 mM peptide in PBS, pH 7.4. 150 μl aliquots were transferred into individual wells of the 10 kDa filter plate (Millipore MAPPB 1010 Biomax membrane). For "0 minutes controls": 270 μl of PBS were placed in a PP tube and 30 μl of stock solution B was added and vortexed. 150 μl of control solution was placed into one well of the filter plate and serves as "filtered control".

Further 150 μl of control solution were placed directly into a receiver well (reserved for filtrate) and serve as "not-filtered control". The entire plate including evaporation lid was incubated for 60 min at 37° C. Plasma samples (rat plasma: Harlan Sera lab UK, human plasma: Blutspendezentrum Zürich) were centrifuged at least for 2 h at 4300 rpm (3500 g) and 15° C. in order to yield 100 μl filtrate. For "serum albumin"-samples (freshly prepared human albumin: Sigma A-4327, rat albumin: Sigma A-6272, all at 40 mg/ml concentration in PBS) approximately 1 hour of centrifugation is sufficient. The filtrates in the receiver PP plate were analysed by LC/MS as follows: Column: Jupiter C18 (Phenomenex), mobile phases: (A) 0.1% formic acid in water and (B) acetonitrile, gradient: 5%-100% (B) in 2 minutes, electrospray ionization, MRM detection (triple quadrupole). The peak areas were determined and triplicate values are averaged. The binding is expressed in percent of the (filtered and not-filtered time point 0 min) control 1 and 2 by: $100-(100*T_{60}/T_0)$. The average from these values is then calculated (see ref. 9 below).

3.0 In Vivo Studies

3.1. Maximum Tolerated Dose in Mice a) The compound of Example 1, dispersed in Water for Injection or 0.9% physiological saline), was administered, in the preliminary study, by i.v. injection at dose levels of 35, 50, 70, 85, 100, 150, 250 or 500 mg/kg to groups consisting of one male and one female mouse (Crl:CD1(ICR)). In addition, two groups comprising two male and two female mice received dose levels of 90 and 100 mg/kg, respectively, and the 50 mg/kg dose level was repeated in a group comprising one male and one female.

b) Maximum tolerated dose studies (MTD) carried out with the compound of Example 2 using CD1 mice (3 mice/group) and was performed using i.v, ip and sc. administration.

3.2 Repeated Toxicity Studies in Mice

The toxicity and toxicokinetics of the compound of Example 1 was investigated following daily i.v. injection in the mouse for at least 14 days. Groups of 12 male and 12 female Crl:CD1(ICR) mice received dose preparations containing control article (50 mM sodium dihydrogen orthophosphate buffer containing 0.9% w/v sodium chloride) or 8, 24, or 40 mg/kg/day POL6326 at a dose volume of 5 mL/kg. Satellite groups of 24 animals per sex per group were included at each dose level. Assessment of toxicity was based on mortality, clinical signs, body weights, food consumption, ophthalmic examinations, clinical and anatomic pathology, and toxicokinetic evaluations.

3.3 Stemcell Mobilisation a) Mice Model:

The aim of the study was to evaluate the ability of the compound of Example 1 and Example 2 to mobilize hematopoietic progenitors from mouse bone marrow to peripheral blood using in-vitro hematopoietic colony assays. In humans, accurate information about progenitor cell mobilization is provided by the colony forming unit granulocyte-monocyte (CFU-GM) assay or by determining the abundance of CD34(+) cells by FACS analysis (see ref. 10 below). In mice, CD34 is not a useful marker for stem cells; instead the CFU-GM is more commonly used (see ref. 11 below).

In order to assess the ability of the compounds of Example 1 and Example 2 to mobilize murine stem cells (CFU-GM) C3H/HeJ female mice (Jackson Laboratory) were injected s.c. with 5 mg/k, of the compounds of Example 1 and of Example 2 and as reference AMD3100 (Broxmeyer, et al, *J Exp Med* 201, 1307-1318), (currently undergoing Phase III clinical trials) for stem cell mobilisation. Peripheral blood samples from 5 animals per test group were collected at each time point and nucleated cell counts performed as standard assays.

b) Monkey Model:

An assessment of mobilization of peripheral-blood hematopoietic stem cells in cynomolgus monkeys (*Macaca fascicularis*) was performed. The compound of Example 1 was administered to 4 monkeys (2 male and 2 female) as a slow bolus i.v. injection over 2 minutes and CD34(+) cells were determined by FACS analysis. Toxicokinetic blood sampling was also performed.

4.0. Results

The results of the experiments described under 2.2-2.8, above, are indicated in the following Tables 1 and 2.

TABLE 1

| Ex. | $IC_{50}$ (nM) $Ca^{2+}$ assay | FIGS IC50 (nM) | Cyto-toxicity $LC_{50}/GI_{50}$ Hela cells | Hemo-lysis at 100 µM | $IC_{50}$ (µM) Cell migration assay |
|---|---|---|---|---|---|
| 1 | 5.5 | n.d. | >50 | 0.6 | n.d. |
| 2 | 4.1 | 24.7 | 94 | 0.3 | 0.5 | n.d.: not determined

TABLE 2

| Ex. | Stability human Plasma $t_{1/2}$ (min) | Stability rat Plasma $t_{1/2}$ (min) |
|---|---|---|
| 1 | >240 | >240 |
| 2 | >300 | >300 |

The results of the experiment described in 3.1-3.3 are given herein below.

4.1: MTD Study in Mice a) MTD Study, Compound of Example 1

The acute minimum lethal intravenous dose level of Ex. 1 in the mouse was found to exceed 90 mg/kg.

b) MTD Study, Compound of Example 2

The highest dose tested for all three routes of administration was 120 mg/kg bolus. At this dose all animals survived and only mild symptoms were observed. The symptoms exhibited were slight behavioral depression, slight cyanosis, an increase in respiratory depth and muscle relaxation.

4.2: 14-Day Intravenous Injection Toxicity and Toxicokinetic Study

The NOAEL level for the compound of Example 1 following i.v. dosing in the mouse was 40 mg/kg/day.

There was no notable effect of treatment on body weight, body weight change, or food consumption, or on ophthalmic observations during the final week of the dosing phase.

Administration of the compound of Example 1 was associated with mildly higher white blood cell and absolute lymphocyte counts for females given 40 mg/kg/day. Males given 40 mg/kg/day were not similarly affected, and these minor effects were not considered adverse. Clinical chemistry results were unaffected by administration of the compound of Example 1. Increases in organ weights (kidneys in males given 8 mg/kg/day and seminal vesicles in males given 24 or 40 mg/kg/day) were considered incidental and unrelated to treatment. No test article-related gross lesions were recorded. Three animals (1 control group female, 1 male at 8 mg/kg/day and 1 female at 24 mg/kg/day) had a focal, red, crusted area at the injection site (tail), which was the result of hypodermic needle punctures. No test article-related microscopic lesions were observed.

Figure 2:
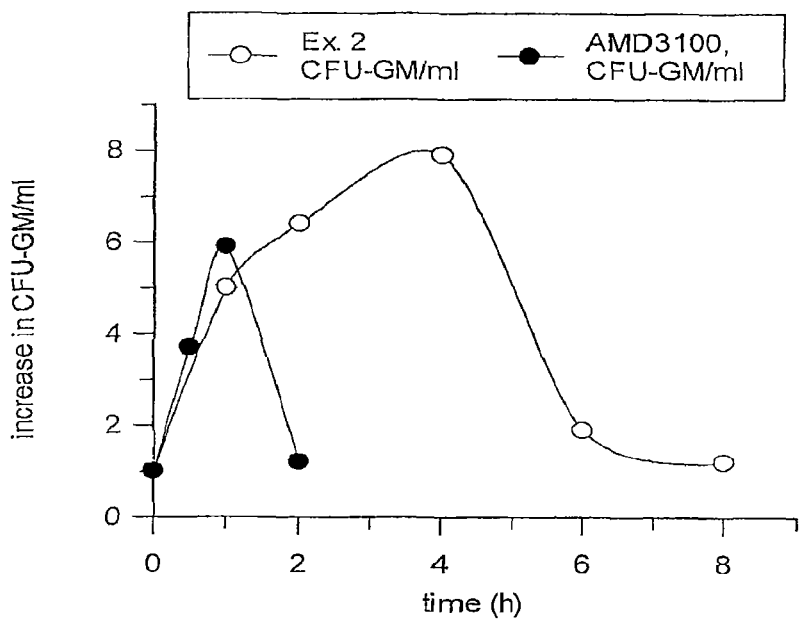
FIG. 2. Increase in Colony Forming Units per ml of blood (CFU-GM) over time for both the compound of Example 2 and the reference compound AMD3100.
Figure 3:
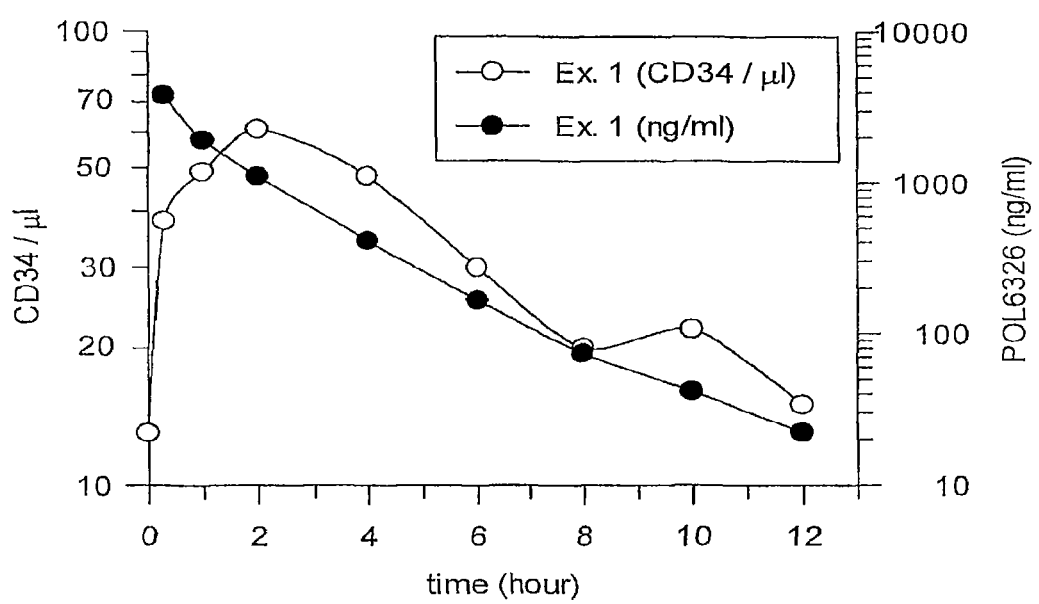
FIG. 3. Average number of CD34(+) cells per μL, of blood over time for compound of Example 1.

4.3: Stemcell Mobilisation a) Stem Cell Mobilization in Mice, Compound of Example 1:

Administration of 5 mg/kg of the compound of Example 1 increased the CFU-GM blood cell numbers with a maximal effect at 120 minutes and return to baseline levels 6 h post administration. (FIG. 1). In the same assay, AMD3100 (currently undergoing Phase III clinical trials for stem cell mobilisation) was used as a comparator. In a follow up study, the dose response of Ex. 1 on the release of CFU-GM was determined (FIG. 1). There is a clear dose response effect of Ex. 1 on the release of CFU-GM in mice with a peak level increase at 5 mg/kg.

b) Stem Cell Mobilization in Mice, Compound of Example 2:

Administration of 5 mg/kg of the compound of Example 2 increased the CFU-GM blood cell numbers up to six hours post administration with a maximal effect at 240 minutes whereas administration of AMD3100 is associated with an increase in the frequency and number of progenitors at 30 and 60 minutes compared to control mice (FIG. 2).

c) Stem Cell Mobilization in Monkey, Compound of Example 1:

Administration of the compound of Example 1 induced mobilization of CD34(+) hematopoietic cells in cynomolgus monkeys. As observed in mice, the onset of mobilization was rapid with a peak level at two hours. The mobilisation was also transient and the numbers of stem cells in peripheral blood returned to baseline level with decreasing plasma levels of the compound of Example 1 (FIG. 3).

REFERENCES

1. Oberlin E, Amara A, Bachelerie F, Bessia C, Virelizier J-L, Arenzana-Seisdedos F, Schwartz O, Heard J-M, Clark-Lewis I, Legler D F, Loetscher M, Baggiolini M, Moser B. *Nature.* 1996, 382:833-835
2. Loetscher M, Geiser T, O'Reilly T, Zwalen R, Baggiolini M, Moser B. *J. Biol. Chem.* 1994. 269:232-237
3. D'Apuuo M, Rolink A, Loetscher M, Hoxie J A, Clark-Lewis I, Melchors F, Baggiolini M, Moser B. *Eur. J. Immunol.* 1997. 27:1788-1793
4. von Tschamer V, Prod'hom B, Baggiolini M, Reuter H. *Nature.* 1986. 324:369-72.
5. Hamy F, Felder E R, Heizmann G, Lazdins J, Aboul-ela F, Varani G, Karn J, Klimkait T. *Proc. Natl. Acad. Sci.* 1997. 94:3548-3553.
6. Mossman T. *J. Immunol. Meth.* 1983, 65:55-63
7. Berridge M V, Tan A S. *Arch. Biochem. Biophys.* 1993, 303:474-482
8. Frevert C W, Wong V A, Goodman R V, Goodwin R, Martin T R, *J. Immunol. Meth.* 1998. 213: 41-52
9. Singh R., Chang, S. Y., Talor, L. C., Rapid Commun. Mass Spectrom., 1996, 10: 1019-1026
10. To L B, Haylock D N, Simmons P J, Juttner C A. Blood 1997, 89(7):2233-2258.
11. Broxmeyer H E, Orschell C M, Clapp D W, Hangoc G, Cooper S, Plett P A et al. J Exp Med 2005. 201(8):1307-1318.

The invention claimed is:

1. A method for treating cancer that expresses a CXCR4 receptor, the method comprising:
   administering a therapeutically effective amount of a Cyclo(-Tyr-His-X-Cys-Ser-Ala-$^D$Pro-Dab-Arg-Tyr-Cys-Tyr-Gln-Lys-$^D$Pro-Pro) compound having a disulfide bond between Cys4 and Cys11, or a pharmaceutically acceptable salt thereof, wherein X is Ala or Tyr to a subject in need thereof.

2. The method of claim 1, wherein the administering is oral, topical, transdermal, injection, buccal, transmucosal, pulmonary or inhalation administration.

3. The method of claim 1, wherein the compound is administered in a composition further comprising a pharmaceutically inert carrier and wherein the composition is in the form of a tablet, a dragee, a capsule, a solution, a liquid, a gel, a plaster, a cream, an ointment, a syrup, a slurry, a suspension, a spray, a nebulizer, or a suppository.

4. The method of claim 1, wherein the cancer is breast cancer.

* * * * *

UNITED STATES PATENT AND TRADEMARK OFFICE
CERTIFICATE OF CORRECTION

PATENT NO. : 9,879,047 B2
APPLICATION NO. : 15/379820
DATED : January 30, 2018
INVENTOR(S) : Daniel Obrecht et al.

It is certified that error appears in the above-identified patent and that said Letters Patent is hereby corrected as shown below:

On the Title Page

(57) ABSTRACT:
"The template-fixed β-hairpin peptidomimetics Cyclo(-Tyr-His-Cys-Ser-Ala-$^D$Pro-Dab-Arg-Tyr-Cys-Tyr-Gln-Lys-$^D$Pro-Pro), disulfide bond between Cys4 and Gys11, and pharmaceutically acceptable salts thereof, with X being Ala or Tyr, have CXCR4 antagonizing properties and can be used for where cancer is mediated or resulting from CXCR4 receptor activity", Should read:
--The template-fixed β-hairpin peptidomimetics Cyclo(-Tyr-His-X-Cys-Ser-Ala-$^D$Pro-Dab-Arg-Tyr-Cys-Tyr-Gln-Lys-$^D$Pro-Pro), disulfide bond between Cys4 and Cys11, and pharmaceutically acceptable salts thereof, with X being Ala or Tyr, have CXCR4 antagonizing properties and can be used for where cancer is mediated or resulting from CXCR4 receptor activity--.

Signed and Sealed this
Ninth Day of July, 2019

Andrei Iancu
*Director of the United States Patent and Trademark Office*